(12) United States Patent
Frenvik et al.

(10) Patent No.: US 10,729,794 B2
(45) Date of Patent: Aug. 4, 2020

(54) ISOTOPE PURIFICATION METHOD

(71) Applicant: BAYER AS, Oslo (NO)

(72) Inventors: Janne Olsen Frenvik, Oslo (NO); Olav B. Ryan, Rasta (NO)

(73) Assignee: BAYER AS, Oslo (NO)

( * ) Notice: Subject to any disclaimer, the term of this patent is extended or adjusted under 35 U.S.C. 154(b) by 0 days.

(21) Appl. No.: 16/067,675

(22) PCT Filed: Dec. 29, 2016

(86) PCT No.: PCT/EP2016/082842
§ 371 (c)(1),
(2) Date: Jul. 2, 2018

(87) PCT Pub. No.: WO2017/118593
PCT Pub. Date: Jul. 13, 2017

(65) Prior Publication Data
US 2019/0001005 A1    Jan. 3, 2019

(30) Foreign Application Priority Data

Jan. 5, 2016    (GB) .................................. 1600161.2

(51) Int. Cl.
| | | |
|---|---|---|
| *A61K 51/10* | (2006.01) | |
| *B01D 15/36* | (2006.01) | |
| *B01J 39/05* | (2017.01) | |
| *B01J 39/17* | (2017.01) | |
| *A61N 5/10* | (2006.01) | |
| *B01J 39/26* | (2006.01) | |
| *C07K 16/32* | (2006.01) | |

(52) U.S. Cl.
CPC ........ *A61K 51/1045* (2013.01); *A61N 5/1001* (2013.01); *B01D 15/362* (2013.01); *B01J 39/05* (2017.01); *B01J 39/17* (2017.01); *B01J 39/26* (2013.01); *C07K 16/32* (2013.01); *A61N 2005/1021* (2013.01)

(58) Field of Classification Search
CPC ...................................................... A61K 51/00
See application file for complete search history.

(56) References Cited

U.S. PATENT DOCUMENTS

2013/0183235 A1*   7/2013   Ramdahl ............ A61K 51/0478
                                                                424/1.53

FOREIGN PATENT DOCUMENTS

| WO | 02/05859 | 1/2002 |
|---|---|---|
| WO | 2004/091668 | 10/2004 |
| WO | WO2014195423 | * 11/2014 |
| WO | 2014/195423 | 12/2014 |

OTHER PUBLICATIONS

International Search Report for PCT/EP2016/082842 dated Mar. 21, 2017, 3 pages.

* cited by examiner

*Primary Examiner* — Michael G. Hartley
*Assistant Examiner* — Jagadishwar R Samala
(74) *Attorney, Agent, or Firm* — Morrison & Foerster LLP

(57) ABSTRACT

The invention provides a method for the purification of 227 Th from a mixture comprising 227 Th and 223 Ra, said method comprising: i) preparing a first solution comprising a mixture of 227 Th and 223 Ra ions dissolved in a first aqueous buffer; ii) loading said first solution onto a separation material such as a strong cation exchange resin; iii) eluting 227 Th from the separation material, whereby to generate a second solution comprising 227 Th; iv) Optionally rinsing said separation material using a first aqueous washing medium; The invention additionally provides a method for forming a radio pharmaceutical comprising complexing the purified 227 Th, the pharmaceutical product and its use in treatment of disease such as cancer and a kit for generation of such a product.

19 Claims, 6 Drawing Sheets

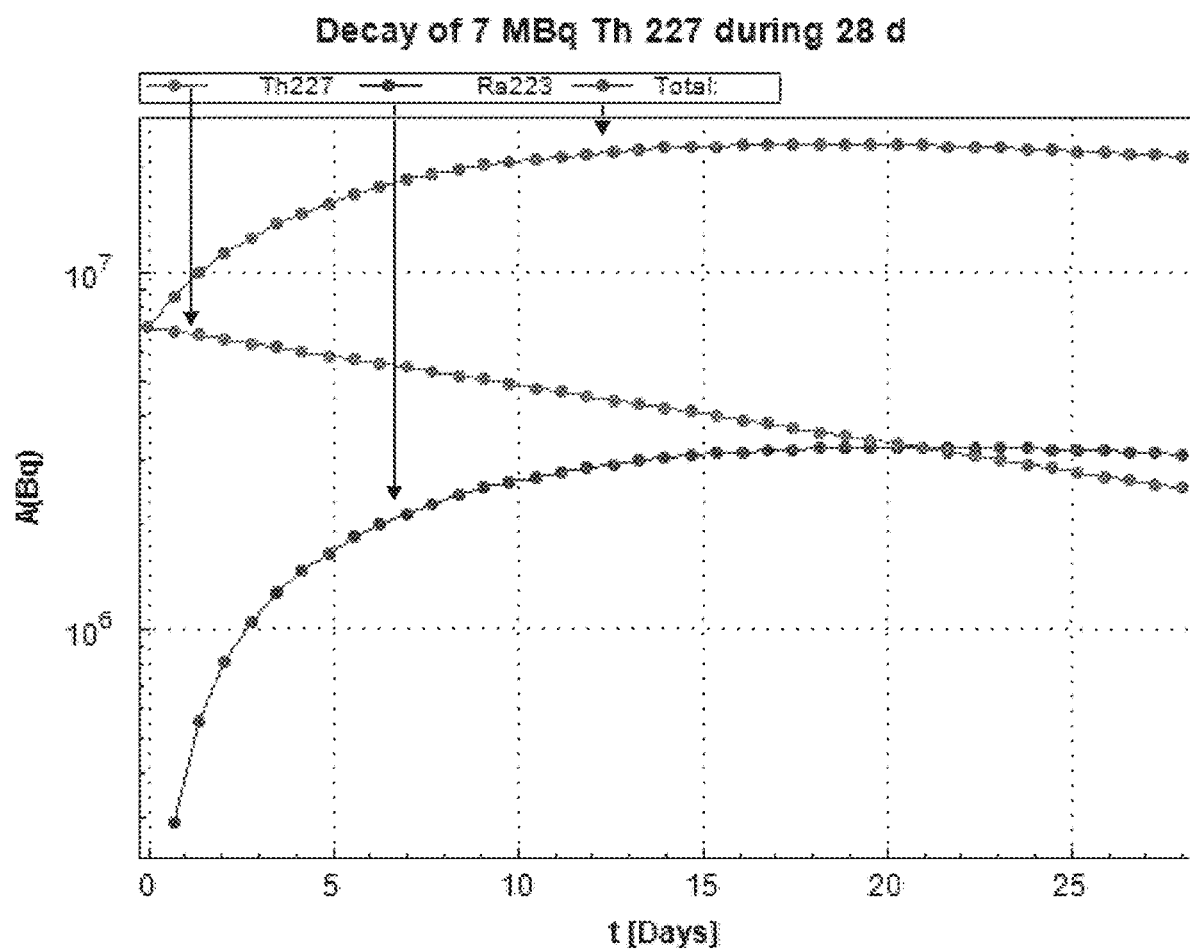
Figure 1 – in-growth of daughter isotopes upon storage of thorium-227

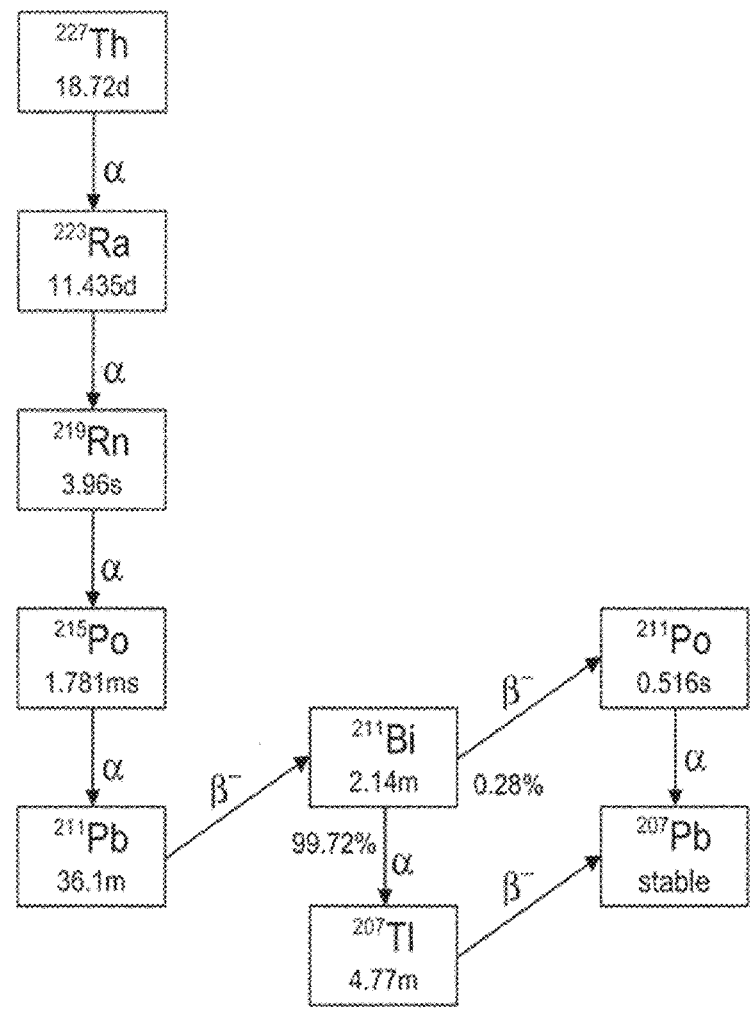
Figure 2 – the decay chain from $^{227}$Th to $^{207}$Pb

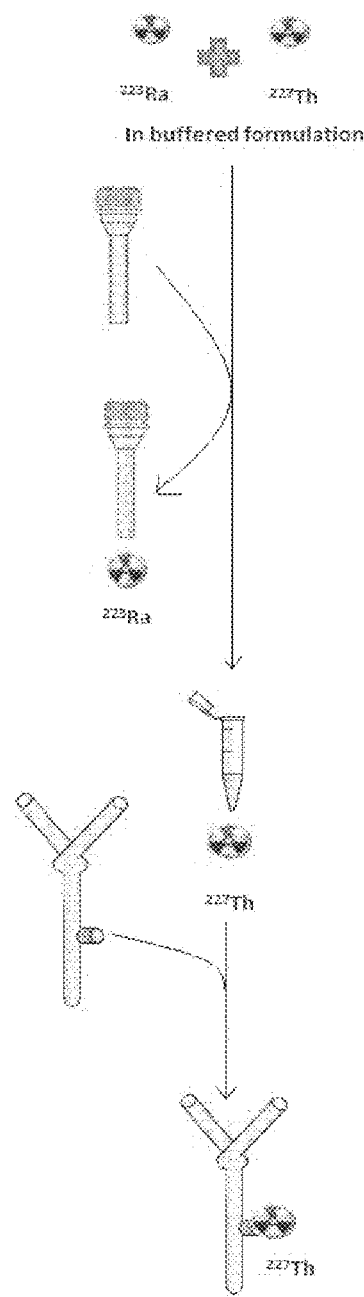
Figure 3 – Purification of decayed $^{227}$Th and preparation of Targeted Thorium Conjugate (TTC);

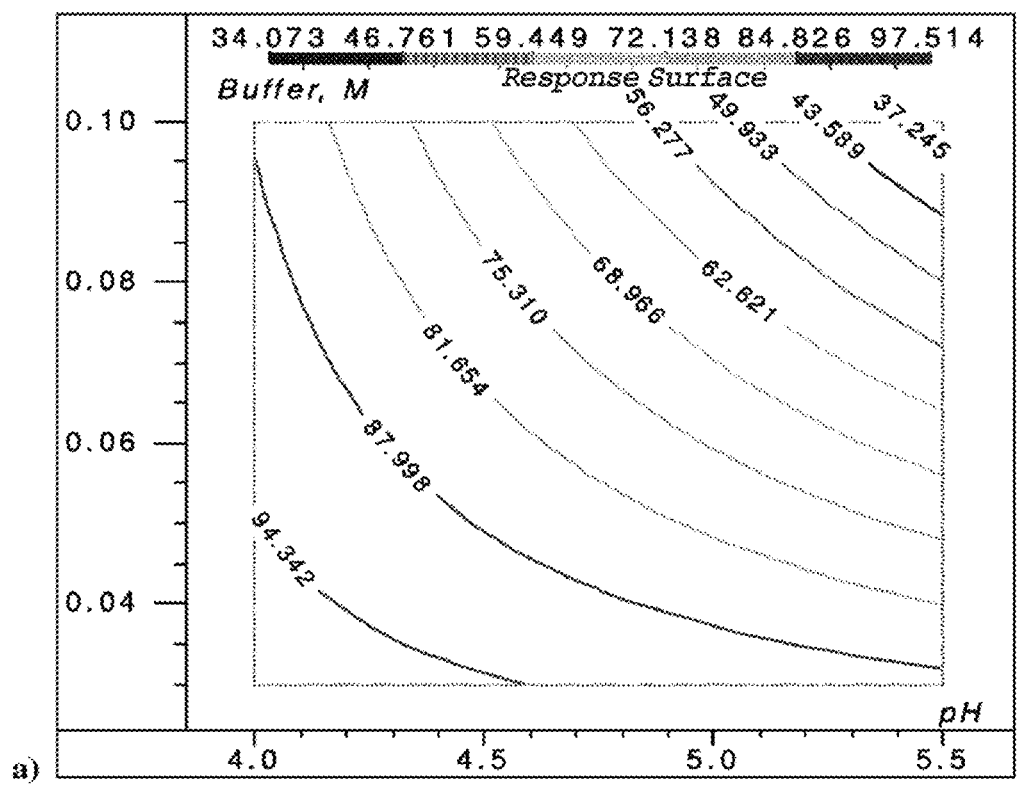
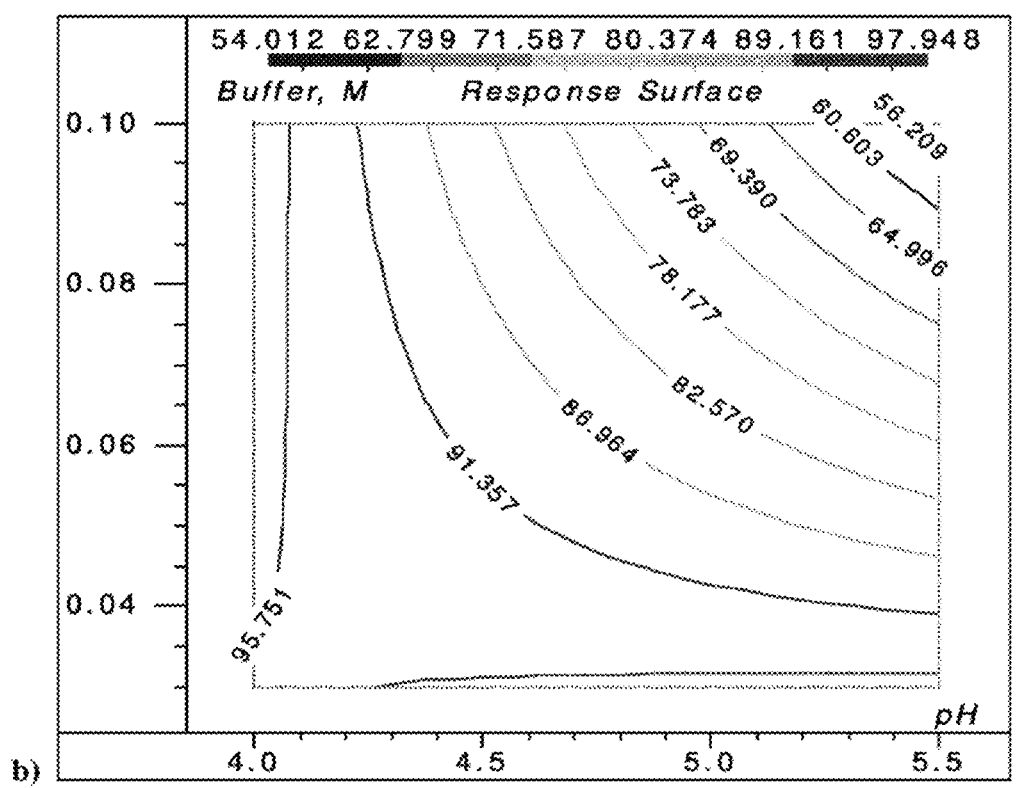
Figure 4 - Effect of varying citrate buffer concentration and pH on uptake of $^{223}$Ra.

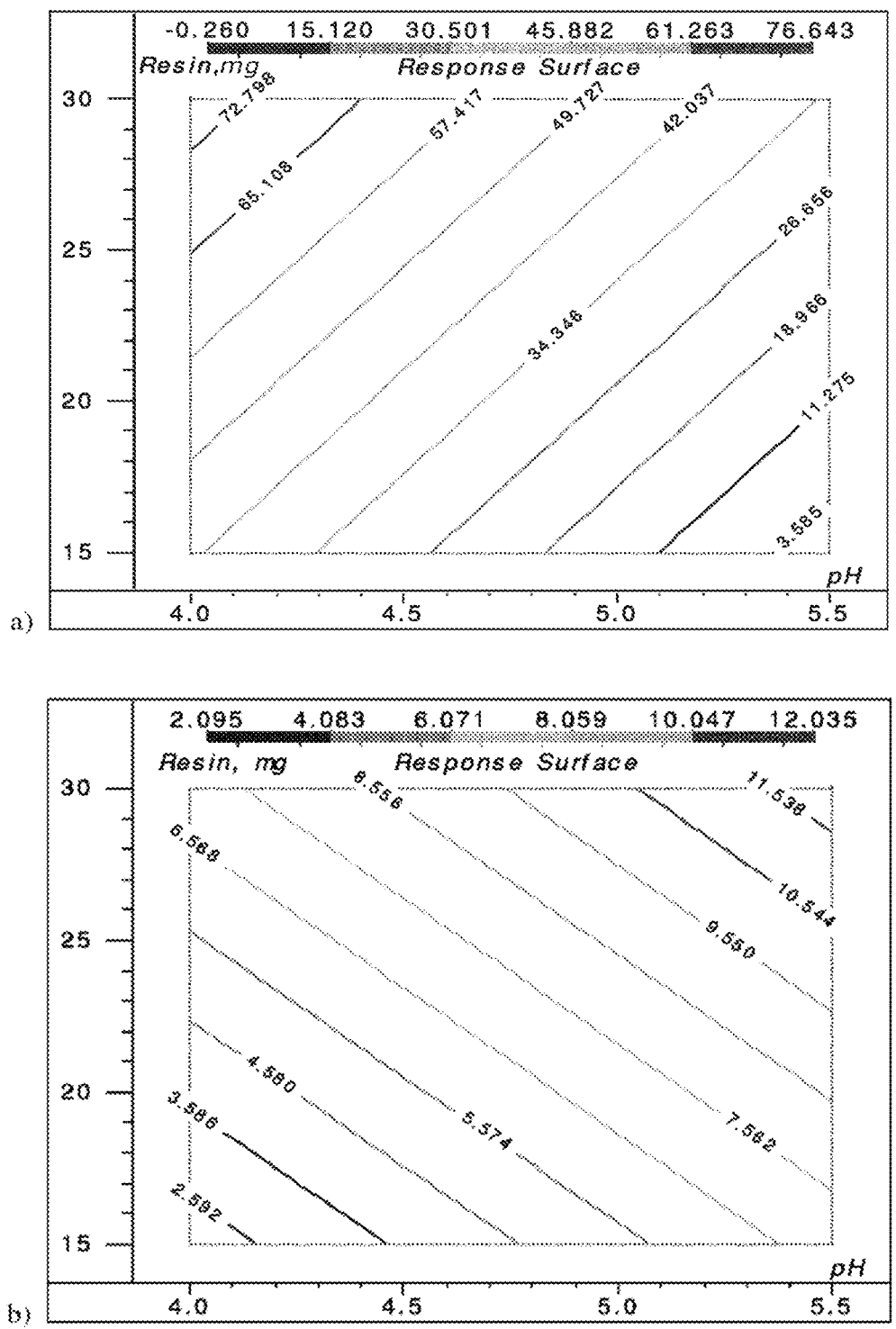
Figure 5 - Effect of varying PSA resin mass and buffer pH on uptake of $^{227}$Th.

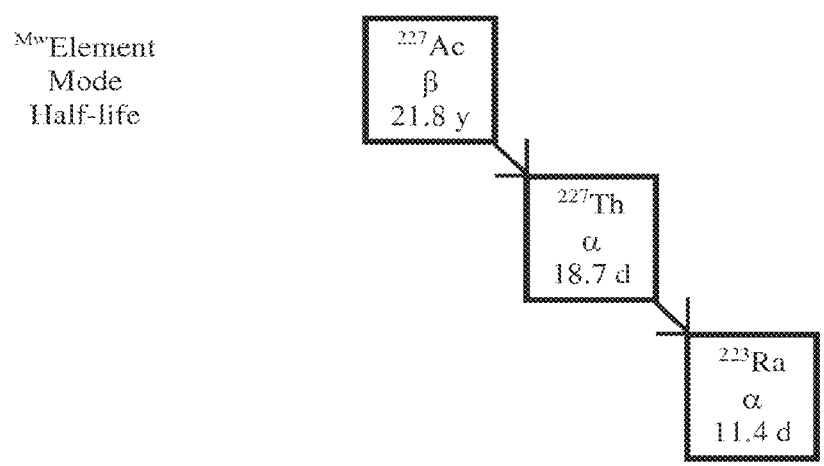
Figure 6 – decay chain from $^{227}$Ac to $^{223}$Ra

ISOTOPE PURIFICATION METHOD

This application is the U.S. national phase of International Application No. PCT/EP2016/082842 filed Dec. 29, 2016 which designated the U.S. and claims priority to GB Patent Application No. 1600161.2 filed Jan. 5, 2016, the entire contents of each of which are hereby incorporated by reference.

FIELD OF THE INVENTION

The present invention relates to the purification of thorium-227 ($^{227}$Th) for pharmaceutical use. In particular, the present invention relates to methods of purification of thorium-227 shortly prior to use in pharmaceutical administration to human subjects.

BACKGROUND TO THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of many other diseases, especially immunological, hyperplastic and/or other neoplastic diseases.

The most common methods of selective treatment are currently surgery, chemotherapy and external beam irradiation. Targeted endo-radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been a recent surge in interest in the use of alpha-emitting radionuclides in therapy because of their potential for more specific cell killing. One alpha-emitting nuclide in particular, radium-223 ($^{223}$Ra) has proven remarkably effective, particularly for the treatment of diseases associated with the bone and bone-surface. Additional alpha-emitters are also being actively investigated and one isotope of particular interest is the alpha-emitter thorium-227.

The radiation range of typical alpha emitters in physiological surroundings is generally less than 100 micrometers, the equivalent of only a few cell diameters. This makes these nuclei well suited for the treatment of tumours, including micrometastases, because little of the radiated energy will pass beyond the target cells and thus damage to surrounding healthy tissue might be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). These properties explain the exceptional cytotoxicity of alpha emitting radionuclides and also impose stringent demands on the level of purity required where an isotope is to be administered internally. This is especially the case where any contaminants may also be alpha-emitters, since these can potentially be retained in the body and cause significant damage. Radiochemical purity should be as high as reasonably feasible and contamination with non-targeted radionuclides should be minimised, particularly where the contaminant is an alpha-emitter.

The radioactive decay chain from $^{227}$Ac, generates $^{227}$Th and then leads to $^{223}$Ra and further radioactive isotopes. The first three isotopes in this chain are shown in FIG. 6. The table shows the element, molecular weight (Mw), decay mode (mode) and Half-life (in years (y) or days (d)) for $^{227}$Th and the isotopes preceding and following it. Preparation of $^{227}$Th can begin from $^{227}$Ac, which is itself found only in traces in uranium ores, being part of the natural decay chain originating at $^{235}$U. One ton of uranium ore contains about a tenth of a gram of actinium and thus although $^{227}$Ac is found naturally, it is more commonly made by the neutron irradiation of $^{226}$Ra in a nuclear reactor.

It can be seen from this illustration that $^{227}$Ac, with a half-life of over 20 years, is a very dangerous potential contaminant with regard to preparing $^{227}$Th from the above decay chain for pharmaceutical use. Even once the $^{227}$Ac is removed or reduced to a safe level, however, $^{227}$Th will continue to decay to $^{223}$Ra with a half-life of just under 19 days. Since $^{223}$Ra is an alkaline earth metal it will not easily be coordinated by ligands designed for thorium or other actinides. This $^{223}$Ra then forms the beginning of a potentially uncontrolled (untargeted) decay chain including 4 alpha-decays and 2 beta-decays before reaching stable $^{207}$Pb. These are illustrated in the table below:

| Nuclide | $^{227}$Th | $^{223}$Ra | $^{219}$Rn | $^{215}$Po | $^{211}$Pb | $^{211}$Bi | $^{207}$Tl | $^{207}$Pb |
|---|---|---|---|---|---|---|---|---|
| ½-life | 18.7 d | 11.4 d | 4.0 s | 1.8 ms | 36.1 m | 2.2 m | 4.8 m | stable |
| α-energy/MeV | 6.15 | 5.64 | 6.75 | 7.39 | | 6.55 | | |
| β-energy (max)/MeV | | | | | 1.37 | | 1.42 | |
| Energy % | 17.5 | 16.0 | 19.1 | 21.0 | 3.9 | 18.6 | 4.0 | |

It is evident from the above two decay tables that $^{223}$Ra cannot be entirely eliminated from any preparation of $^{227}$Th because the latter will constantly be decaying and generating the former. It is clear, however, that more than 25 MeV in radiated energy will be released from the decay of each $^{223}$Ra nucleus administered to a patient, before that nucleus reaches a stable isotope. It is also probable that such $^{223}$Ra will not be bound and targeted by the systems of chelation and specific binding designed to transport $^{227}$Th to its site of action, due to the differing chemical nature of the two elements. Therefore, for the purpose of targeted cell killing, maximising the therapeutic effect and minimising side-effects, it is important to have control over the level of $^{223}$Ra in any $^{227}$Th preparation prior to administration.

Separation of $^{227}$Th from $^{223}$Ra could be carried out quickly and conveniently in a radiological laboratory. However, this would not achieve the desired result effectively because the resulting purified $^{227}$Th must then be transported to the site of administration.

In view of the above, it would be a considerable advantage to provide a method of purifying $^{227}$Th from contaminant $^{223}$Ra which could be carried out at or close to the point-of-care, at or shortly before the time of administration utilising a simple method that would not require extensive training and experience to carry out. It would be an advantage if the use of strong mineral acids and/or strong bases could be avoided from a safety and handling point of view. This applies particularly if the reagents used are suitable for direct use in the final drug product. It would also be an advantage if small volumes could be used to ease handling and reduce the volume of contaminated waste. It would be a further advantage if this method could be implemented with a simple group of reagents and items of apparatus, which could be supplied for such a contemporaneous preparation, optionally in the form of a kit.

Previously known preparations for $^{227}$Th have generally been for laboratory use and/or not tested for purity to pharmaceutical standards. In WO2004/091668, for example, $^{227}$Th was prepared by anion exchange from a single column and used for experimental purposes without validation of the purity. The primary aim of separation in most preparative methods for $^{227}$Th has been the removal of the long-lived $^{227}$Ac parent isotope. Methods have not previously been devised or optimised for removal of $^{223}$Ra which has grown-in in a $^{227}$Th sample previously purified from $^{227}$Ac.

BRIEF DESCRIPTION OF THE INVENTION

The present inventors have now established that a quick and simple purification procedure may be used to remove $^{223}$Ra from a preparation of $^{227}$Th using a single cation exchange purification step. In this way, a $^{227}$Th solution of very high radiochemical purity may be produced while providing a number of desirable advantages in the method.

In a first aspect, the present invention therefore provides a method for the purification of $^{227}$Th from a mixture comprising $^{227}$Th and $^{223}$Ra, said method comprising:
i) preparing a first solution comprising a mixture of $^{227}$Th and $^{223}$Ra ions dissolved in a first aqueous buffer;
ii) loading said first solution onto a separation material (e.g. strong cation exchange resin);
iii) eluting $^{227}$Th from said separation material whereby to generate a second solution comprising $^{227}$Th;
iv) Optionally rinsing said separation material using a first aqueous washing medium;

Generally the steps i) to iv) will be carried out in the order given above, although other steps and processes may evidently be carried out during or between the listed steps.

The process will optionally also include at least one of the following further steps, each generally conducted after steps i) to iv) above:
v) assaying for the $^{227}$Th content of said second solution;
vi) evaporating the liquid from said second solution;
vii) forming at least one radiopharmaceutical from at least a portion of the $^{227}$Th contained in said second solution;
viii) sterilising (e.g. sterile filtering) said radiopharmaceutical.

Step vii) forms a particularly preferably additional step.

In a further aspect, the present invention provides a solution or other sample of $^{227}$Th comprising less than 50KBq $^{223}$Ra per 1MBq $^{227}$Th, preferably less than 10KBq $^{223}$Ra per 1MBq $^{227}$Th. Such a solution is optionally formed or formable by any of the methods herein described, and is preferably formed or formable by the preferred methods herein described. Correspondingly, the methods of the invention are preferably for the formation of a solution of of $^{227}$Th comprising less than 50KBq $^{223}$Ra per 1MBq $^{227}$Th, preferably less than 10KBq $^{223}$Ra per 1MBq $^{227}$Th. A corresponding pharmaceutical preparation is also provided, which may be sterile and may comprise at least one complexing agent (especially for $^{227}$Th), at least one targeting agent (e.g. conjugated to said complexing agent), and optionally at least one pharmaceutically acceptable carrier or diluent.

In a still further aspect, the invention also provides a kit (typically a kit for carrying out a method of the invention) comprising a mixture of $^{227}$Th and $^{223}$Ra, a first aqueous buffer, and a separation material (e.g. cation exchange resin). The mixture of $^{227}$Th and $^{223}$Ra (as with the first solution in other aspects of the invention) will typically also comprise further $^{223}$Ra daughter products. Such a mixture may be the result of radioactive decay of purified or partially purified $^{227}$Th during storage and/transportation.

DETAILED DESCRIPTION OF THE INVENTION

Pharmaceuticals of all types must routinely be produced to a very high standard of purity and a very high confidence that standards (e.g. of purity and sterility) have been met. Administration of an alpha-emitting radionuclide to the body of a subject requires all of these considerations but additionally adds a need for high radiochemical purity. Purification from long-lived precursor isotopes is one key aspect of radiochemical purity but this can typically be accomplished in a specialist radiochemical laboratory or factory where complex methods and handling procedures can be utilised.

A further level of radiochemical purification may be necessary, however, in the event that the radionuclide of interest decays to other radioactive isotopes. The generation of radioactive daughter isotopes may contribute significantly to the toxicity of endo-radionuclide therapy and can be dose-limiting. In the case of $^{227}$Th, the daughter isotope is radium, an alkaline earth metal, while the parent is a transition metal of the actinide series. This means that any chelation or complexation which may have been suitable for binding thorium will probably not be chemically suitable for retaining the daughter radium. Alpha decay additionally imparts a very significant "recoil" energy onto the daughter nucleus as a result of conservation of momentum following ejection of an alpha particle at very high speeds. This recoil carries many times more energy than a covalent bond or coordinating interaction and will inevitably shunt the daughter nucleus out of the immediate environment of the original parent isotope.

Since the presence of $^{223}$Ra and its daughters generated in vivo by $^{227}$Th decay is potentially dose-limiting, it is important that no (significant) additional, unnecessary, $^{223}$Ra is administered to the subject to further limit the acceptable therapeutic dose of $^{227}$Th or to exaggerate the side effects.

The present invention has been developed in view of the inevitable in-growth of $^{223}$Ra into a $^{227}$Th sample and the desire to minimise that $^{223}$Ra delivered to the subject, as far as reasonably possible. Since $^{223}$Ra will initially grow in at a rate of around 0.2% of the total activity per hour, the method should be carried out no more than a few hours before administration in order to minimise the unnecessary dose. Similarly, if the $^{227}$Th can be used within 2-4 hours of preparation then the method should preferably provide $^{227}$Th with around 99% (e.g. 95% to 99.9%) radiochemical purity with respect to $^{223}$Ra. Higher purity may be inefficient and/or insignificant since ingrowth before use will undo any benefits of a more stringent purification method while lower purity (say less than 90% or less than 95% radiochemical purity) is undesirable because the dose of $^{223}$Ra (and thus toxicity) could reasonably be further limited while allowing for a realistic administration time.

In one embodiment, the mixtures of $^{227}$Th and $^{223}$Ra for use in the present invention will contain no significant amount of radioactive isotopes that are not in the decay chain beginning at $^{227}$Th. In particular, the mixtures of $^{227}$Th and $^{223}$Ra for use in any of the aspects of the present invention will preferably comprise less than 20 Bq $^{227}$Ac per 100MBq $^{227}$Th, preferably less than 5 Bq $^{227}$Ac per 100MBq $^{227}$Th.

The present invention provides a method for the production of $^{227}$Th at a purity level suitable for use in endoradionuclide therapy. A number of preferred features of the system are indicated below, each of which may be used in combination with any other feature where technically viable, unless explicitly indicated otherwise.

The methods and all corresponding embodiments of the invention will preferably be carried out on a scale suitable for patient administration. This scale may be that if a single therapeutic dose, or may be that suitable for a number of subjects, each receiving a dose. Typically the method will be used at a scale suitable for administration within 1 to 5 hours, such as around 1 to 10 typical doses of $^{223}$Ra. Single-dose purification forms one preferred embodiment. Evidently, a typical dose will depend upon the application, but it is anticipated that a typical dose may be from 0.5 to 100 MBq, preferably 1 to 25 MBq, most preferably around 1.2 to 10 MBq. Pooled dosage purification will be carried out where possible, using up to 20, preferably up to 10 or up to 5 typical doses. Purification my thus be carried out with up to 200 MBq, preferably up to 100 MBq and divided into separate doses after purification, as appropriate.

Step i) of the method of the invention relates to solution comprising $^{227}$Th and $^{223}$Ra (and will commonly also comprise $^{223}$Ra daughter isotopes—see those tabulated above). Such a mixture will inherently form by the gradual decay of a sample of $^{227}$Th, but for use in the invention will preferably also have one or more of the following features, either individually or in any viable combination:
a) The $^{227}$Th radioactivity may be at least 0.5 MBq (e.g. 0.5 MBq to 200 MBq), preferably at least 0.5 MBq, more preferably at least 1.2 MBq;
b) The solution may be formed in a first aqueous buffer solution;
c) The solution may have a volume of no more than 50 ml (e.g. 0.5 to 10 ml or 0.5 to 5 ml), preferably no more than 10 ml or 5 ml, more preferably no more than 3 ml.
d) The first aqueous buffer solution may be at a pH of between 3 and 6.5, preferably between 3.5 and 6, and particularly between 3.8 and 5.8.
e) The first aqueous buffer solution may be used at a concentration of 0.01 to 0.2 M, such as 0.03 to 0.05 M or 0.1 to 0.2 M.
f) The first aqueous buffer solution may comprise, consist essentially of or consist of at least one organic acid buffer.
g) The first aqueous buffer solution may comprise, consist essentially of or consist of at least one organic acid buffer selected from citrate buffer, acetate buffer and mixtures thereof.
h) The first aqueous buffer solution may optionally additionally comprise at least one free radical scavenger and/or at least one chelating agent (especially a non-buffering chelating agent). Many of each are known in the art and include pABA (scavenger) and EDTA (chelator).
i) The first aqueous buffer solution may optionally additionally comprise other additives including salts, such as NaCl.

Step ii) of the method of the invention relates to the loading of the first solution onto a separation material (e.g. cation exchange resin). This step and the entities referred to therein may have the following preferable features, either individually or in any viable combination, and optionally in any viable combination with any of the features of the other steps as described herein:
a) The separation material may be a cation exchange resin or hydroxyapatite, preferably a strong cation exchange resin.
b) The resin (e.g. strong cation exchange resin) may be silica based resin;
c) The cation exchange resin may comprise one or more acid functional groups;
d) The cation exchange resin may comprise at least one acid moiety and preferably at least one carboxylic acid or sulphonic acid moiety, such as an alkyl sulphonic acid resin such as a propylsulphonic acid (PSA) resin;
e) The resin (e.g. strong cation exchange resin) may have an average particle size of 5 to 500 µm, preferably 10 to 200 µm.
f) The separation material (e.g. cation exchange resin) may be used in the form of a column.
g) The amount of separation material (e.g. resin) used (e.g. when packed in a column) may be 100 mg or less, (e.g. 2 to 50 mg), preferably 10 to 50 mg.
h) The separation material (e.g. resin) may be pre-conditioned by washing with one or more volumes of an aqueous medium prior to loading with the first solution. Generally a buffer solution, and more preferably the first aqueous buffer will be used for pre-conditioning.

Step iii) of the method of the invention relates to eluting $^{227}$Th from said separation material (e.g. strong cation exchange resin) whereby to generate a second solution comprising $^{227}$Th. This step and the entities referred to therein may have the following preferable features, either individually or in any viable combination, and optionally in any viable combination with any of the features of the other steps as described herein:
a) The elution may be by means of an eluent solution or by means of "dry" elution, such as by elution under gravity, under centrifugal force or under gas pressure from above and/or vacuum from below;
b) Where elution is by means of an eluent solution, this may be an aqueous buffer solution, such as any of those described herein, including organic acid buffer solutions;
c) The elution may be by "dry" means, preferably under gravitational or centrifugal force, such as spinning in a centrifuge.
d) elution by centrifugal force may be at a "relative centrifugal force" (RCF) of at least 1000, preferably at least 2000 or at least 10000 times the force of gravity (e.g. an rcf of 1000 to 50000 g) for a period of 10 seconds to 10 minutes, preferably 20 seconds to 5 minutes;

Step iv) of the method of the invention relates to the optional step of rinsing said separation material (e.g. strong cation exchange resin) using a first aqueous washing medium. This step and the entities referred to therein may have the following preferable features, either individually or in any viable combination, and optionally in any viable combination with any of the features of the other steps as described herein:
a) The first aqueous washing medium may be water, such as distilled water, deionised water or water for injections or may be a buffer such as an organic acid buffer as described herein;
b) The first aqueous washing medium may comprise the same buffer as the first buffer solution;
c) The optional washing step may be omitted;
d) The optional washing step may comprise adding a first washing medium to the resin following "dry" elution as described here and then "dry" eluting the washing medium, such as by gravity or centrifugation;
e) The solution eluted in the washing step may be combined with the second solution comprising $^{227}$Th.

Following step iv) of the method of the invention, the separation material (e.g. resin) will typically be disposed of as radioactive waste. Since the amount of resin required is typically quite small (e.g. less than 50 mg), this does not present a major disposal issue. If, however, it is desired to re-use the resin or to recover the $^{223}$Ra for assay or any other reason, the $^{223}$Ra may be eluted using any suitable medium. Suitable media for such recovery include buffer solutions, such as those described herein and aqueous mineral acids, such as HCl and $H_2SO_4$. If the resin is to be re-used then it will typically be regenerated with several volumes of the first buffer solution prior to re-use.

The methods of the present invention may comprise a number of optional steps, each of which may be present or absent independently so far as technically possible.

Step v) of the method of the invention relates to optionally assaying for the $^{227}$Th content of the second solution. This step and the entities referred to therein may have the following preferable features, either individually or in any viable combination, and optionally in any viable combination with any of the features of the other steps as described herein:
a) $^{227}$Th may be assayed by gamma detection/spectroscopy, such as by use of a germanium semiconductor detector (high purity germanium detector—HPGe);
b) $^{227}$Th content may be compared to a desired pharmaceutical dose and diluted to a standard concentration, or an appropriate dose withdrawn for administration.

Step vi) of the method of the invention relates to the optional step of evaporating the liquid from said second solution. This step may be desirable where the final pharmaceutical composition has a low volume. Typically, the first aqueous buffer will be selected such that it is compatible with the labelling reaction (as described herein) and is physiologically tolerable (i.e. suitable for injection at the concentrations and amounts used). In this way, concentration step vi) will preferably be avoided. Where necessary, this step may be included and the entities referred to therein may have the following preferable features, either individually or in any viable combination, and optionally in any viable combination with any of the features of the other steps as described herein:
a) The evaporation may be conducted under reduced pressure (e.g. 1 to 500 mbar).
b) The evaporation may be conducted at elevated temperature (e.g. 50 to 200° C., preferably 80 to 110° C.);

Step vii) of the method of the invention relates to the optional step of forming at least one radiopharmaceutical from at least a portion of the $^{227}$Th purified by means of steps i) to iv). This step and the entities referred to therein may have the following preferable features, either individually or in any viable combination, and optionally in any viable combination with any of the features of the other steps as described herein. Furthermore, all of the features of the radiopharmaceutical indicated herein form preferred features of the pharmaceutical aspect of the present invention, particularly where that pharmaceutical is formed or formable by a method of the invention:
a) The portion of the $^{227}$Th from said second sample (purified by means of steps i) to iv)) may be 1 MBq to 100 MBq, preferably from 1 to 10 MBq.
b) The radiopharmaceutical may comprise at least one complexing agent.
c) The complexing agent may comprise an octadentate ligand.
d) The complexing agent may comprise a hydroxypyridinone such as hydroxypyridinone (HOPO) ligand, preferably an octadentate 3,2-hydroxypyridinone (3,2-HOPO).
e) The radiopharmaceutical may comprise a targeting moiety.
f) The targeting moiety may be an antibody, antibody construct, antibody fragment (e.g. FAB or F(AB)'2 fragment or any fragment comprising at least one antigen binding region(s)), or a construct of such fragments.
g) The targeting moiety may be a receptor or receptor binder (e.g. a hormone, vitamin, folate or a folate analogue) a bisphosphonate or nano-particle.
h) The targeting moiety may have specificity for at least on disease-associated antigen such as a "cluster of differentiation" (CD) cell surface molecule (e.g. CD22, CD33, CD34, CD44, CD45, CD166 etc).
i) The targeting moiety may be linked to the ligand moiety by a covalent linker whereby to form a targeting conjugate.
j) The method of formation may comprise incubating the portion of the $^{227}$Th contained in said second sample with the targeting conjugate. Such incubation may be at a temperature below 50° C., preferably 10 to 40° C., such as 20 to 30° C. Such incubation may be for a period of less than 2 hours, such as 1 minute to 60 minutes (e.g. 1 to 15 minutes), preferably 15 to 45 minutes.
k) Pharmaceutical carriers, diluents, buffers, salts, preservatives etc may be added whereby to form an injectable radiopharmaceutical.
l) The complexed $^{227}$Th from said second solution may be diluted to a standard activity based upon the activity measurements obtained in step v), optionally correcting for the period between preparation and administration.

The radiopharmaceutical formed or formable in the various aspects of the present invention may be used in the treatment of any suitable disease, such as a neoplastic or hyperplastic disease (e.g. a carcinoma, sarcoma, melanoma, lymphoma, or leukemia). The pharmaceutical formulation, both as such and for such a use, as well as the corresponding methods of treatment of a subject form further aspects of the invention. Such a subject will typically be in need thereof, such as a subject suffering from a neoplastic or hyperplastic disease (e.g. those described herein). The invention will further provide for a method of administration of a radiopharmaceutical to a subject (e.g. one in need thereof) comprising forming said radiopharmaceutical by steps i) to iv), vii) and optionally any of steps v), vi) and/or viii) and administering said radiopharmaceutical (e.g. by intravenous injection or directly to a specific tissue or site) to said subject.

Step viii) of the method of the invention is an optional step comprising sterile filtering the solution or pharmaceutical (especially that formed in step vii)). This step and the entities referred to therein may have the following preferable features, either individually or in any viable combination, and optionally in any viable combination with any of the features of the other steps as described herein:
a) The filtration may be through a suitable membrane, such as a 0.22 µm (or smaller) membrane.
b) The filtration may be by syringe through a suitable syringe filter.

In addition to the above steps, the methods of the invention and all corresponding aspects may comprise additional steps, for example to validate the purity of the $^{227}$Th for pharmaceutical purposes, to exchange counter-ions, concentrate or dilute the solution or to control factors such as pH and ionic strengths. Each of these steps thus forms an optional but preferable additional step in the various aspects of the present invention.

It is preferable that the methods of the present invention provide for a high yield of the $^{227}$Th product. This is not only because of the desire to avoid wastage or a valuable product but also because all lost radioactive material forms radioactive waste which must then be disposed of safely. Thus, in one embodiment, at least 50% (e.g. 50 to 90% or 50% to 98%) of the $^{227}$Th loaded in step ii) is eluted in step iv). This will preferably be at least 70%, more preferably at least 80% and most preferably at least 85% yield.

In a corresponding aspect of the present invention, there is additionally provided pharmaceutical composition comprising the $^{227}$Th and optionally at least one pharmaceutically acceptable diluent. Such a pharmaceutical composition may comprise $^{227}$Th of a purity indicated herein, optionally formed or formable by the methods of the present invention. Suitable carriers and diluents including water for injection, pH adjusters and buffers, salts (e.g. NaCl) and other suitable materials will be well known to those of skill in the art.

The pharmaceutical composition will comprise the $^{227}$Th as described here, typically as an ion, such as the Th$^{4+}$ ion. Such compositions may comprise a simple salt of the $^{227}$Th of the invention but will more preferably comprise a complex of the $^{227}$Th of the invention with at least one ligand, such as an octadentate 3,2-hydroxypyridinone (3,2-HOPO) ligand. Suitable ligands are disclosed in WO2011/098611, which is hereby incorporated by reference, particularly with reference to formulae I to IX disclosed therein, which represent typical suitable HOPO ligands. Such ligands may be used in themselves or conjugated to at least one targeting moiety, such as an antibody. Antibodies, antibody constructs, fragments of antibodies (e.g. FAB or F(AB)'2 fragments or any fragment comprising at least one antigen binding region(s)), constructs of fragments (e.g. single chain antibodies) or a mixture thereof are particularly preferred. The pharmaceutical compositions of the invention may thus comprise Th$^{4+}$ ion of $^{227}$Th of pharmaceutical purity as disclosed herein, complexed to a conjugate of a 3,2-hydroxypyridinone (3,2-HOPO) ligand and at least one antibody, antibody fragment or antibody construct, plus optionally pharmaceutically acceptable carriers and/or diluents. The embodiments described herein with respect to the pharmaceutical composition will also form embodiments of the corresponding method where practicable and vice versa.

As used herein, the term "comprising" is given an open meaning such that additional components may optionally be present (thus disclosing both "open" and "closed" forms). In contrast the term "consisting of" is given a closed meaning only, such that (to an effective, measurable and/or absolute degree), only those substances indicated (including any optional substances as appropriate) will be present. Correspondingly, a mixture or substance described as "consisting essentially of" will in essence consist of the stated components such that any additional components do not affect the essential behaviour to any significant extent. Such mixtures may, for example, contain less than 5% (e.g. 0 to 5%) of other components, preferably less than 1% and more preferably less than 0.25% of other components. Similarly, where a term is given as "substantially", "around", "about" or "approximately" a given value, this allows for the exact value given, and independently allows for a small variability, particularly where this does not affect the substance of the property described. Such variability may be, for example ±5% (e.g. ±0.001% to 5%), preferably ±1%, more preferably ±0.25%.

The invention will now be illustrated further by reference to the following non-limiting examples and the attached figures, in which:

FIG. 1 Shows the decay of $^{227}$Th over time and the corresponding in-growth of $^{223}$Ra and daughter isotopes over 90 days.

FIG. 2 Shows the radioactive decay chain of $^{227}$Th to stable $^{207}$Pb via $^{223}$Ra.

FIG. 3 Shows the purification and labelling steps carried out shortly before administration in order to separate $^{227}$Th from in-grown $^{223}$Ra and complex the purified $^{227}$Th to an antibody/ligand conjugate.

FIG. 4 Shows the effect of buffer concentration (M) (y-axis) and pH (x-axis) on uptake of $^{223}$Ra from citrate buffered formulations at 15.0 mg resin (a) and 30.0 mg resin (b).

FIG. 5 Shows the effect of pH (x-axis) and resin amount (mg) (y-axis) on uptake of $^{227}$Th from acetate buffered formulations without additives (a) and with pABA and EDTA (b).

FIG. 6 Shows the radioactive decay chain of $^{227}$Ac to $^{223}$Ra.

The following legends apply to the corresponding Figures of this application:

FIG. 3—Purification of decayed $^{227}$Th and preparation of Targeted Thorium Conjugate (TTC); sequestering of $^{223}$Ra from buffered formulation by purification on micro-spin column, followed by labelling of purified 227Th on conjugate (antibody with chelator)

FIG. 4—Effect of varying citrate buffer concentration and pH on uptake of $^{223}$Ra (in percentage) onto (a) 15.0 mg and (b) 30.0 mg of PSA resin.

FIG. 5—Effect of varying PSA resin mass and buffer pH on uptake of $^{227}$Th (in percentage) onto PSA from acetate buffer a) without additives pABA/EDTA and b) with pABA/EDTA additives.

EXAMPLES

Materials

Sodium acetate trihydrate (≥99.0%), Sodium citrate tribasic dihydrate, (≥99.0%), 4-aminobenzoic acid sodium salt (pABA, ≥99%), Edetate disodium (EDTA, meets USP testing specifications), and sodium hydroxide (98.0-100.5%) were purchased from Sigma-Aldrich (Oslo, Norway). Metal free water (TraceSELECT) was purchased from FLUKA (Buchs, Switzerland). Sodium chloride (for analysis), hydrochloric acid (fuming, 37%, for analysis) and acetic acid (glacial, 100% anhydrous for analysis) was purchased from Merck Millipore (Darmstadt, Germany). Citric acid monohydrate (analytical reagent) was purchased from VWR (West Chester, USA). PSA (propylsulphonic acid) cation exchange resin based on silica was purchased from Macherey Nagel (Düren, Germany). NAP5 columns were purchased from GE Healthcare Bio-Sciences AB (Uppsala, Sweden). Micro-Spin Columns were purchased from Thermo Scientific Pierce (product number 89879 (Rockford, USA).

The conjugate was an in house product and consisted of 5 mg/ml trastuzumab in sodium citrate buffer 0.10 M pH 5.5 and 0.90% (w/w) sodium chloride. The conjugate was made from an in house chelator attached to the trastuzumab antibody. Trastuzumab from Herceptin® (150.0 mg powder for concentrate for solution for infusion) is a trademark of Roche Registration Limited (Welwyn Garden City, Great Britain).

The available radioactivity source was decayed $^{227}$Th (as thorium(IV)) in 0.05 M hydrochloric acid and metal free water (an in house product). $^{227}$Th was left to decay for approximately one half-life of 19 days until which the quantity of $^{223}$Ra (as radium(II)) builds up to a near 1:1 ratio of $^{227}$Th and $^{223}$Ra.

Example 1—Preparation of Buffered Formulations

Stock citrate buffers (0.10 M pH 4.0, 0.10 M pH 5.5, 0.05 M pH 5.0, and 0.07 M pH 4.8) and stock acetate buffers (0.10 M pH 4.0, 0.10 M pH 6.0, 0.10 M pH 5.5, 0.07 M pH 4.8, and 0.10 M pH 5.0) were prepared in metal free water and further diluted if required. pABA (2.0 mg/ml) and EDTA (2.0 mM) was subsequently added to selected formulations. In addition, selected citrate buffered formulations were added sodium chloride (0.45 or 0.90% (w/w) to adjust ionic strength.

All excipients used are included in the inactive ingredient list from FDA for approved drug products suitable for i.v. injection.

A calibrated sevenMulti pHmeter from Mettler Toledo (Oslo, Norway) was used to measure pH of stocks and final formulations at ambient temperature.

Example 2—Preparation of Micro-Spin Columns with PSA Cation Exchange Resin 1500.00 mg PSA silica resin was suspended in 15.00 ml metal free water. The suspension was shaken on a vortex mixer to ensure homogeneity before the appropriate volume was transferred to the micro-spin columns to give a resin amount of 15.0, 22.5, and 30.0 mg, respectively. The columns were subsequently spun for 1 minute at 10000 rcf to remove the water by an Eppendorf thermomixer comfort (Hamburg, Germany).

The columns were conditioned with 300 µl of the respective buffered formulations. The excess volume was removed by spinning for 1 minute at 10000 rcf on the thermomixer resulting in dry columns (n=2 for DOE samples and center points).

Example 3—Purification

600 µl of the respective buffered formulations was mixed with approximately 400 kBq $^{227}$Th and 400 kBq $^{223}$Ra in 0.05 M hydrochloric acid (i.e. 1-5 µl decayed $^{227}$Th in hydrochloric acid, dependent on the radioactive concentration). Half the volume was subsequently added to each column (n=2). The columns were then spun for 1 minute at 10000 rcf on the thermomixer, leaving the columns dry. The eluate was collected in an Eppendorf tube below the column.

Example 4—Radioassay

The amount of $^{223}$Ra and $^{227}$Th on the cation exchange columns and in the eluates after the separation method of Example 3 was measured before calculating the distribution of the radionuclides between the column and the eluate. HPGe spectra from a High Purity Germanium (HPGe)-detector (GEM(15) from Ortec (Oak Ridge, Tenn.) was used. This detector identifies and quantifies radionuclides with gamma energies ranging from approximately 30 to 1400 keV. All samples analyzed by the HPGe-detector were placed in the same position and counted for 1 min. This method could be used to assay the radioisotope concentration in the eluate prior to preparing the radiopharmaceutical both to ensure a standard activity and to validate radiochemical (radioisotope) purity.

Example 5—Labelling of Trastuzumab Conjugate with Purified $^{227}$Th

350 µl of the respective buffered formulations was mixed with approximately 1000 kBq $^{227}$Th and 1000 kBq $^{223}$Ra in 0.05 M hydrochloric acid (i.e. 1-5 µl decayed $^{227}$Th in hydrochloric acid, dependent on the radioactive concentration). Half the volume was added to each micro-spin column (n=2). The columns were then for spun 1 minute at 10000 rcf on the thermomixer, leaving the columns dry with the eluate in an Eppendorf tube below the column. The amount of $^{227}$Th and $^{223}$Ra on the cation exchange columns and in the eluates was measured with the High Purity Germanium (HPGe)-detector GEM(15) before calculating the amount of $^{227}$Th in the eluate for further use to label the conjugate.

A frozen sample of the trastuzumab-chelator conjugate (5.00 mg/ml) was allowed to equilibrate to ambient temperature. 160 µl of the conjugate was then transferred to an Eppendorf tube and mixed with 160 µl eluate in selected citrate buffered formulations from the micro-spin columns (approximately 500 kBq $^{227}$Th). The formulations tested were 0.10 M citrate buffer pH 5.5 and the equivalent buffered formulation containing pABA+EDTA (n=2). The samples were then shaken for 30 minutes (22° C., 750 rpm, 10 s cycles) on the thermomixer.

Example 6—Validation of the Labelling Reaction

The radiochemical purity (RCP) of a radiopharmaceutical is the relationship between $^{227}$Th (in this case) present in a bound form (the TTC) to $^{227}$Th in its unbound form (free radionuclide). The RCP was calculated by adding 200 µl of the respective labelled conjugated sample (TTC) to a NAP5 column and, following the standard procedure for the column given by the manufacturer, the amount of 227Th uptake on the NAP5 column (size exclusion chromatography) and in the eluate was analysed by the aid of the HPGe-detector spectra (n=2).

According to Bayer AS standards, a successful labelling reaction will give a radiochemical purity above 90% for the TTC (Monoclonal Antibody and Peptide-Targeted Radiotherapy of Cancer, Wiley, 2010.). The labelling of trastuzumab conjugate with purified decayed 227Th was within requirements for both the formulation containing 0.10 M citrate buffer pH 5.5 and the equivalent formulation also containing pABA+EDTA (n=2).

Example 7—Separation Optimisation

A Design of Experiment (DOE) was devised to investigate and optimise the conditions for separation of $^{223}$Ra from $^{227}$Th on a silica/PSA micro spin column. For each buffer (citrate and acetate), the following variables were investigated:

TABLE 1

| DoE variable | Denomination | Span |
|---|---|---|
| pH | A | 4.0-5.5 |
| pABA (2 mg/ml) + EDTA (2 mM) | B | w/wo (with or without) |
| Buffer concentration (M) | C | 0.03 ± 0.10 |
| Resin mass (mg) | D | 15.0 ± 30.0 |

Each of the DoE variables was investigated using the separation methodology indicated in Examples 1 to 6. The results are shown in FIGS. 4 and 5, which illustrate the effect of various parameters on radioisotope uptake onto PSA resin.

Optimal separation conditions were found to be:

TABLE 2

| Formulation | PH | pABA/EDTA w or w/o | Buffer conc., M | Resin mass, mg | Predicted $^{227}$Th, % | Predicted $^{223}$Ra, % |
|---|---|---|---|---|---|---|
| Citrate | 4.0 | w or w/o | 0.03 | 15.0 | 2.4 | 97.5 |
| Acetate | 4.0 | w* | 0.03-0.10 | 15.0 | 1.6 | 96.2 |

*According to Pooled SD and response surface the uncertainty is expected to be lower with than without pABA/EDTA

The invention claimed is:

1. A method for purification of $^{227}$Th from a mixture comprising $^{227}$Th and $^{223}$Ra, said method comprising:
  i) preparing a first solution comprising a mixture of $^{227}$Th and $^{223}$Ra ions dissolved in a first aqueous buffer, wherein said first aqueous buffer is at a pH of between 3 and 6.5 and comprises at least one organic acid buffer selected from the group consisting of citrate buffer, acetate buffer and mixtures thereof;
  ii) loading said first solution onto a cation exchange resin;
  iii) eluting $^{227}$Th from said cation exchange resin to generate a second solution comprising $^{227}$Th;
  iv) assaying for $^{227}$Th content of said second solution;
  v) evaporating the liquid from said second solution;
  vi) forming at least one radiopharmaceutical from at least a portion of the $^{227}$Th contained in said second solution; and
  vii) sterile filtering said radiopharmaceutical wherein said portion of the $^{227}$Th contained in said second solution is between 0.1 MBq and 100 MBq.

2. The method of claim 1, wherein said first aqueous buffer further comprises at least one radical scavenger, at least one chelating agent, or a mixture thereof.

3. The method of claim 1, wherein said cation exchange resin is a silica based resin.

4. The method of claim 1, wherein said cation exchange resin comprises at least one $CH_2$—$SO_3H$ moiety.

5. The method of claim 1, wherein said eluting is by drying.

6. The method of claim 1, wherein said method does not comprise any additional washing steps.

7. The method of claim 1, further comprising washing said cation exchange resin using a first aqueous washing medium.

8. The method of claim 1, further comprising assaying for the $^{227}$Th content of said second solution by gamma detection or gamma spectroscopy.

9. The method of claim 1, wherein said radiopharmaceutical is formed from said portion of $^{227}$Th and at least one octadentate complexing agent.

10. The method of claim 9, wherein said octadentate complexing agent is conjugated to a targeting moiety selected from the group consisting of an antibody, antibody construct, antibody fragment construct of antibody fragments, nanoparticle, and bisphosphonate.

11. The method of claim 10, wherein said radiopharmaceutical, targeting moiety, or radiopharmaceutical and targeting moiety has specificity for at least one target of cluster of differentiation (CD) cell surface markers.

12. The method of claim 1, wherein said forming comprises incubating said portion of the $^{227}$Th contained in said second solution with a targeting conjugate comprising a complexing agent linked to a targeting moiety at a temperature below 50° C.

13. The method of claim 12, wherein said incubating is carried out for a period of less than 2 hours.

14. The method of claim 13, wherein said incubating is carried out in said first aqueous buffer.

15. The method of claim 1, wherein said eluting is under gravitational or centrifugal force.

16. The method of claim 15, wherein said eluting is by centrifugal force at a relative centrifugal force (RCF) of at least 5000 times the force of gravity.

17. The method of claim 15, wherein said eluting is by centrifugal force for a period of 10 seconds to 10 minutes.

18. The method of claim 1, wherein said eluting is under gas pressure from above, vacuum from below, or a combination thereof.

19. The method of claim 8, wherein said assaying for the $^{227}$Th content of said second solution is by use of a germanium semiconductor detector.

* * * * *